(12) United States Patent
Sawhney et al.

(10) Patent No.: US 10,940,231 B2
(45) Date of Patent: *Mar. 9, 2021

(54) SUPERABSORBENT, FREEZE DRIED HYDROGELS FOR MEDICAL APPLICATIONS

(71) Applicant: Incept, LLC, Lexington, MA (US)

(72) Inventors: Amarpreet S. Sawhney, Lexington, MA (US); Steven L. Bennett, Cheshire, CT (US); Suresh S. Pai, Mountain View, CA (US); Scott R. Sershen, Redwood City, CA (US); Fred H. Co, Santa Clara, CA (US)

(73) Assignee: Incept, LLC, Lexington, MA (US)

( * ) Notice: Subject to any disclaimer, the term of this patent is extended or adjusted under 35 U.S.C. 154(b) by 201 days.

This patent is subject to a terminal disclaimer.

(21) Appl. No.: 14/327,245

(22) Filed: Jul. 9, 2014

(65) Prior Publication Data

US 2014/0341836 A1 Nov. 20, 2014

Related U.S. Application Data

(63) Continuation of application No. 11/465,791, filed on Aug. 18, 2006, now Pat. No. 8,795,709.

(60) Provisional application No. 60/743,944, filed on Mar. 29, 2006.

(51) Int. Cl.
*A61L 24/00* (2006.01)
*A61L 24/04* (2006.01)
*A61L 24/10* (2006.01)
*A61B 17/00* (2006.01)

(52) U.S. Cl.
CPC ......... *A61L 24/0031* (2013.01); *A61L 24/046* (2013.01); *A61L 24/10* (2013.01); *A61B 2017/0065* (2013.01)

(58) Field of Classification Search
CPC .... A61L 24/0031; A61L 24/046; A61L 24/10; A61B 2017/0065
See application file for complete search history.

(56) References Cited

U.S. PATENT DOCUMENTS

| | | |
|---|---|---|
| 4,002,173 A | 1/1977 | Manning |
| 4,472,542 A | 9/1984 | Nambu |
| 4,664,857 A | 5/1987 | Nambu |
| 4,734,097 A | 3/1988 | Tanabe et al. |
| 4,826,945 A | 5/1989 | Cohn et al. |
| 4,863,456 A * | 9/1989 | Stephens ............ A61K 9/0004 604/892.1 |
| 4,938,763 A | 7/1990 | Dunn et al. |
| 5,108,421 A | 4/1992 | Fowler |
| 5,376,375 A | 12/1994 | Rhee et al. |
| 5,409,703 A | 4/1995 | McAnalley et al. |
| 5,410,016 A | 4/1995 | Hubbell et al. |
| 5,456,693 A | 10/1995 | Conston et al. |
| 5,462,990 A | 10/1995 | Hubbell et al. |
| 5,510,418 A | 4/1996 | Rhee et al. |
| 5,514,379 A | 5/1996 | Weissleder et al. |
| 5,541,234 A | 7/1996 | Unger et al. |
| 5,550,187 A | 8/1996 | Rhee et al. |
| 5,580,923 A | 12/1996 | Yeung et al. |
| 5,583,114 A | 12/1996 | Barrows et al. |
| 5,627,233 A | 5/1997 | Hubbell et al. |
| 5,643,464 A | 7/1997 | Rhee et al. |
| 5,672,662 A | 9/1997 | Harris et al. |
| 5,700,477 A | 12/1997 | Rosenthal et al. |
| 5,714,159 A | 2/1998 | Shalaby |
| 5,718,916 A | 2/1998 | Scherr |
| 5,744,545 A | 4/1998 | Rhee et al. |
| 5,752,974 A | 5/1998 | Rhee et al. |
| 5,785,679 A | 7/1998 | Abolfthi et al. |
| 5,826,584 A | 10/1998 | Schmitt |
| 5,843,743 A | 12/1998 | Hubbell et al. |

(Continued)

FOREIGN PATENT DOCUMENTS

| | | |
|---|---|---|
| EP | 0732109 | 9/1996 |
| EP | 1704878 | 9/2006 |

(Continued)

OTHER PUBLICATIONS

BusinessDictionary.com, Machining, (acessed Feb. 16, 2016), pp. 1-2.*

(Continued)

*Primary Examiner* — Brian-Yong S Kwon
*Assistant Examiner* — Lyndsey M Beckhardt
(74) *Attorney, Agent, or Firm* — Peter S. Dardi; Diane E. Bennett

(57) ABSTRACT

Methods are provided for making freeze dried hydrogel and structures therefrom that may be introduced into a patient's body for medical applications. Precursor components are combined to initiate crosslinking. The combined precursor components are placed in a chilled tray, and allowed to crosslink to a desired level of complete crosslinking before and/or after being placed onto the tray. The partially crosslinked hydrogel is frozen and freeze dried. After freeze drying, the hydrogel is conditioned to substantially complete crosslinking, and formed into one or more structures, e.g., plugs, hemostatic, or other medical devices. For example, the hydrogel may be cut, machined, rolled, folded, compressed, and/or cored into that may be loaded into delivery devices that may be introduced into a body to implant or otherwise deliver the structures into the body, e.g., to seal a puncture or other passage through tissue.

24 Claims, 5 Drawing Sheets

(56) References Cited

U.S. PATENT DOCUMENTS

| | | | |
|---|---|---|---|
| 5,849,412 A | 12/1998 | Bromberg et al. | |
| 5,874,500 A | 2/1999 | Rhee et al. | |
| 5,932,462 A | 8/1999 | Harris et al. | |
| 5,948,429 A | 9/1999 | Bell et al. | |
| 5,948,829 A | 9/1999 | Wallajapet et al. | |
| 5,951,967 A * | 9/1999 | Golz | A61K 8/03 424/401 |
| 5,955,549 A | 9/1999 | Chang et al. | |
| 5,972,375 A | 10/1999 | Truter et al. | |
| 5,973,014 A | 10/1999 | Funk et al. | |
| 6,051,248 A | 4/2000 | Sawhney et al. | |
| 6,056,768 A | 5/2000 | Cates et al. | |
| 6,063,061 A | 5/2000 | Wallace et al. | |
| 6,083,522 A | 7/2000 | Chu | |
| 6,100,346 A | 8/2000 | Jamiolkowski et al. | |
| 6,129,761 A | 10/2000 | Hubbell | |
| 6,133,325 A | 10/2000 | Schwartz et al. | |
| 6,152,943 A | 11/2000 | Sawhney | |
| 6,162,241 A | 12/2000 | Coury et al. | |
| 6,166,130 A | 12/2000 | Rhee et al. | |
| 6,251,382 B1 | 6/2001 | Greenwald et al. | |
| 6,258,351 B1 | 7/2001 | Harris | |
| 6,261,544 B1 | 7/2001 | Coury et al. | |
| 6,271,278 B1 | 8/2001 | Park et al. | |
| 6,294,183 B1 * | 9/2001 | Ito et al. | 424/404 |
| 6,312,725 B1 | 11/2001 | Wallace et al. | |
| 6,371,975 B2 | 4/2002 | Cruise et al. | |
| 6,379,373 B1 | 4/2002 | Sawhney et al. | |
| 6,458,147 B1 | 10/2002 | Cruise et al. | |
| 6,458,156 B1 | 10/2002 | Wan et al. | |
| 6,458,889 B1 | 10/2002 | Trollsas et al. | |
| 6,495,127 B1 | 12/2002 | Wallace et al. | |
| 6,514,534 B1 | 2/2003 | Sawhney | |
| 6,517,824 B1 | 2/2003 | Kohn et al. | |
| 6,544,276 B1 | 4/2003 | Azizi | |
| 6,566,406 B1 | 5/2003 | Pathak et al. | |
| 6,592,614 B2 | 7/2003 | Lenker et al. | |
| 6,599,515 B1 | 7/2003 | Delmotte | |
| 6,605,294 B2 | 8/2003 | Sawhney et al. | |
| 6,608,117 B1 | 8/2003 | Gvozdic | |
| 6,610,033 B1 | 8/2003 | Melanson et al. | |
| 6,613,070 B2 | 9/2003 | Redmond et al. | |
| 6,632,457 B1 | 10/2003 | Sawhney | |
| 6,639,014 B2 | 10/2003 | Pathak et al. | |
| 6,673,093 B1 | 1/2004 | Sawhney | |
| 6,699,261 B1 | 3/2004 | Cates et al. | |
| 6,703,047 B2 | 3/2004 | Sawhney et al. | |
| 6,774,151 B2 | 8/2004 | Malmgren et al. | |
| 6,818,018 B1 | 11/2004 | Sawhney | |
| 6,863,924 B2 | 3/2005 | Ranganathan et al. | |
| 6,887,974 B2 | 5/2005 | Pathak | |
| 6,916,857 B2 | 7/2005 | Won et al. | |
| 6,923,986 B2 | 8/2005 | Pathak et al. | |
| 6,960,617 B2 | 11/2005 | Omidian et al. | |
| 6,962,979 B1 | 11/2005 | Rhee | |
| 7,001,410 B2 | 2/2006 | Fisher et al. | |
| 7,332,566 B2 | 2/2008 | Pathak et al. | |
| 2002/0081565 A1 * | 6/2002 | Barnea | C12N 1/04 435/2 |
| 2002/0106409 A1 | 8/2002 | Sawhney et al. | |
| 2002/0120228 A1 | 8/2002 | Maa et al. | |
| 2003/0012734 A1 | 1/2003 | Pathak et al. | |
| 2003/0051735 A1 | 3/2003 | Pavcnik et al. | |
| 2004/0033479 A1 * | 2/2004 | Rayner-Brandes et al. | 435/2 |
| 2004/0063206 A1 | 4/2004 | Rowley et al. | |
| 2004/0093015 A1 | 5/2004 | Ogle | |
| 2004/0121905 A1 * | 6/2004 | Ranganathan | A61L 15/425 502/402 |
| 2004/0147016 A1 | 7/2004 | Rowley et al. | |
| 2004/0208892 A1 * | 10/2004 | Evans et al. | 424/195.17 |
| 2004/0249342 A1 | 12/2004 | Khosravi et al. | |
| 2004/0267308 A1 | 12/2004 | Bagaoisan et al. | |
| 2005/0169882 A1 | 8/2005 | Lowe et al. | |
| 2006/0034930 A1 | 2/2006 | Khosravi et al. | |
| 2006/0047313 A1 | 3/2006 | Khanna et al. | |
| 2006/0099238 A1 | 5/2006 | Khosravi et al. | |

FOREIGN PATENT DOCUMENTS

| | | |
|---|---|---|
| EP | 1967220 | 9/2008 |
| WO | 94/01483 | 1/1991 |
| WO | 97/39781 | 10/1997 |
| WO | 98/12274 | 3/1998 |
| WO | 98/35631 | 8/1998 |
| WO | 99/03454 | 1/1999 |
| WO | 99/08718 | 2/1999 |
| WO | 00/09190 | 2/2000 |
| WO | 00/12018 | 3/2000 |
| WO | 00/14155 | 3/2000 |
| WO | 00/19912 | 4/2000 |
| WO | 01/66038 | 9/2001 |
| WO | 02/064182 | 8/2002 |

OTHER PUBLICATIONS

Kang et al. "Fabrication of Porous Gelatin Scaffolds for Tissue Engineering", Biomaterials, vol. 20:1339-1344 (1999).

The Proceedings Of Chemical Society of Japan, vol. 85(2):1033 (2005).

Japanese Office Action with English Translation dated Nov. 6, 2012.

Japanese Office Action with English Translation dated Jul. 18, 2013.

Ariens et al., "Role Of Factor XIII In Fibrin Clot Formation And Effects Of Genetic Polymorphisms", Blood, vol. 100(3):743-754 (Aug. 1, 2002).

Xue et al., "Rapid swelling and deswelling of thermoreversible hydrophobically modified poly(N-isopropylacrylamide) hydrogels prepared by freezing polymerisation", Polymer, 43:5181-5186 (2002).

Xue et al., "Rapid swelling and deswelling in cryogels of cross-linked poly(N-isopropylacrylamide-co-acrylic)". Eueopean Polymer Journal, 40:703-712 (2004).

Notice of Opposition from corresponding European Patent No. 2010236, 13 pages, dated May 29, 2019.

* cited by examiner

SUPERABSORBENT, FREEZE DRIED HYDROGELS FOR MEDICAL APPLICATIONS

CROSS-REFERENCE TO RELATED APPLICATIONS

This application is a continuation of U.S. patent application Ser. No. 11/465,791 filed Aug. 18, 2006 which claims priority to U.S. Provisional Application No. 60/743,944, filed Mar. 29, 2006, which are hereby incorporated by reference herein.

FIELD OF THE INVENTION

The present invention relates generally to hydrogel materials and methods for making such materials, and, more particularly to freeze dried hydrogel materials, methods for making such materials, methods for forming such materials into devices or structures for medical applications and/or for introducing such devices or structures into a body, and to devices and methods for delivering such materials into a body, e.g., to line and/or seal punctures, body lumens, or other passages in a body.

BACKGROUND

Hydrogels are materials that absorb solvents (such as water), undergo rapid swelling without discernible dissolution, and maintain three-dimensional networks capable of reversible deformation. Hydrogels may be uncrosslinked or crosslinked. Uncrosslinked hydrogels are able to absorb water but do not dissolve due to the presence of hydrophobic and hydrophilic regions.

SUMMARY OF THE INVENTION

The present invention is directed to hydrogel materials and methods for making such materials. More particularly, the present invention is directed to methods for making superabsorbent and/or freeze dried hydrogel materials, and to forming such materials into devices or structures for introduction into a body. In addition, the present invention is directed to devices and methods for delivering such materials into a patient's body, e.g., to line and/or seal punctures, body lumens, or other passages in a body.

In accordance with one embodiment, a superabsorbent biodegradable hydrogel is provided, which may be formed by crosslinking precursor components. The hydrogel may be formed by a process including freeze drying or "lyophilizing" the hydrogel before crosslinking is complete. The hydrogel may be crosslinked in an aqueous phase, e.g., by covalent crosslinking. In exemplary embodiments, the polymerization mechanisms used may be electrophilic-nucleophilic or free radical initiated. The hydrogel may be degradable when implanted in tissue or otherwise within a body, e.g., by hydrolysis, or substantially non-degradable. In one embodiment, the hydrogel comprises at least one macromolecular and/or polymeric species, e.g., one or more poly-ethylene glycol (PEG) based molecules, a protein, or polysaccharide. For example, a highly branched active PEG precursor may be mixed with an oligopeptide with two or more lysine groups, e.g., di-, tri-, or tetra-lysine, to form the hydrogel.

In accordance with yet another embodiment, a method is provided for making freeze dried hydrogel that includes combining precursor components to initiate crosslinking of the precursor components to form a hydrogel, freezing the hydrogel when a desired percentage of complete crosslinking is achieved, freeze drying the hydrogel until a desired amount of moisture is removed from the hydrogel, and forming the hydrogel into one or more structures. In one embodiment, the hydrogel may be partially crosslinked before freezing, and crosslinking may be completed after freeze drying, e.g., by one or more conditioning steps or processes. In another embodiment, the hydrogel may be partially crosslinked before freezing, and crosslinking may be completed during freeze drying. In still another embodiment, crosslinking may be completed after freeze drying and/or conditioning.

In accordance with still another embodiment, a method is provided for making hydrogel that includes forming a mixture by combining precursor components to initiate crosslinking of the precursor components to form a hydrogel. The combined precursor components, mixture, and/or hydrogel may be placed onto a tray or other container chilled to a predetermined chilled temperature, e.g., below the freezing point of the combined precursor components. The combined precursor components or mixture may be allowed to crosslink before and/or after being placed on the container.

The hydrogel may be frozen in the container, e.g., by exposing the hydrogel and/or container to a freezing temperature below the freezing point of the combined precursor components for a predetermined freezing duration. The hydrogel may be frozen when a predetermined percentage of complete crosslinking is achieved, e.g., less than one hundred percent complete. As used herein, "complete crosslinking" is defined as having occurred after sufficient time has elapsed at which the hydrogel has substantially no unreacted reactive ester end groups that can enable further crosslinking.

The frozen hydrogel may then be freeze dried until a desired amount of moisture is removed from the hydrogel. Freeze drying may be completed in single or multiple successive stages, e.g., including different and/or variable freeze drying temperatures and/or vacuum pressures. After freeze drying, the hydrogel may be formed into one or more structures. For example, the hydrogel may be rolled, folded, compressed, cored, and/or machined into the one or more structures.

Optionally, before its intended medical use, the hydrogel may be conditioned after freeze drying, e.g., before or after being formed into one or more structures. Conditioning the hydrogel may include one or more stages of exposing the hydrogel to a controlled temperature and/or humidity environment for a predetermined duration, drying the hydrogel using heat, exposing the hydrogel to a controlled gas environment for a predetermined duration, exposing the hydrogel to an aerosolized buffer solution for a predetermined duration, and/or desiccating the hydrogel. The hydrogel may be conditioned during a single stage or during multiple successive stages, e.g., to achieve one or more desired performance characteristics for the final structure(s). In one embodiment, crosslinking of the hydrogel may be completed during the one or more stages of conditioning, e.g., such that the final hydrogel is fully crosslinked to the extent that the hydrogel no longer has a substantial amount of unreacted ester end groups available for further crosslinking.

Varying the degree of crosslinking in the hydrogel at the time of freezing may allow adjustment of the overall morphology of the macroporous network formed after freeze drying when processing the composition. Therefore, partially crosslinking hydrogels before freeze drying may provide various advantages. For example, the pore size, pore quantity, pore distribution, density, and/or physical structure of the polymer network formed after freeze drying a partially crosslinked hydrogel are parameters that may be optimized to suit specific requirements or applications. Manipulation of these parameters by partially crosslinking the hydrogel before freezing may enable the control of performance or functionally desired material properties. These properties may include, but are not limited to, tensile strength, compressive modulus, shear strength, creep resistance, stress relaxation, rate of hydrogel swelling, and/or magnitude of hydrogel swelling. In one embodiment, a low to moderate amount of crosslinking at the time of freezing the hydrogel may yield a low to moderate density, softer, more flexible macroporous polymer network capable of rapid, higher magnitude swelling upon exposure to an aqueous environment. In another embodiment, a moderate to high amount of crosslinking at the time of freezing the hydrogel may yield a moderate to high density, stiffer porous or microporous polymer network capable of gradual, lower magnitude swelling upon exposure to an aqueous environment. These types of materials may be desirable and advantageous for use in various medical applications. Further, adjustment or variation of the degree of crosslinking at the time of freezing may facilitate fabrication and/or processing of compositions with inherent performance capabilities adapted or tailored to provide desired material properties and to fulfill desired performance requirements of individual medical applications.

Other aspects and features of the present invention will become apparent from consideration of the following description taken in conjunction with the accompanying drawings.

DETAILED DESCRIPTION

Figure 1:
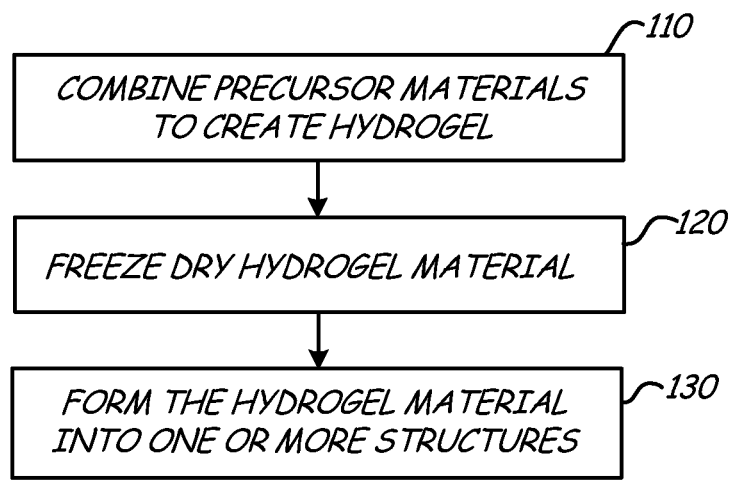
FIGS. 1-3 are flowcharts, showing exemplary methods for making freeze dried hydrogel.
Figure 2:
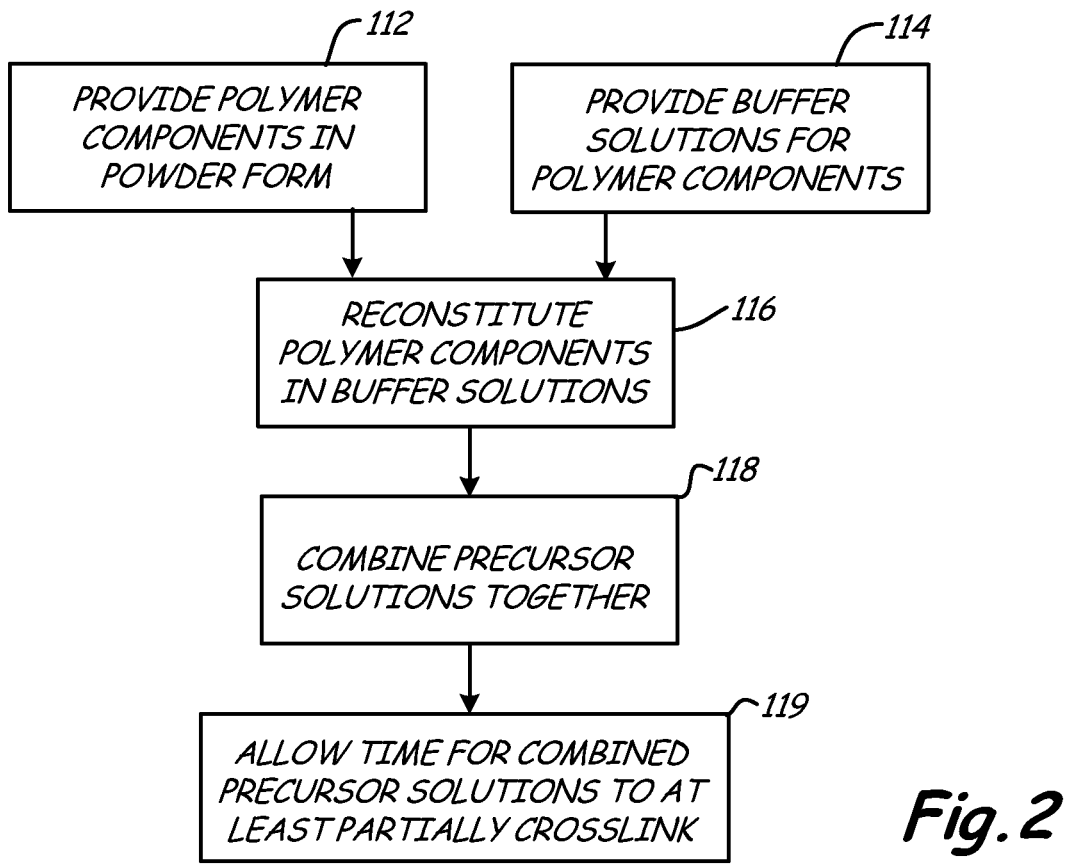
Figure 3:
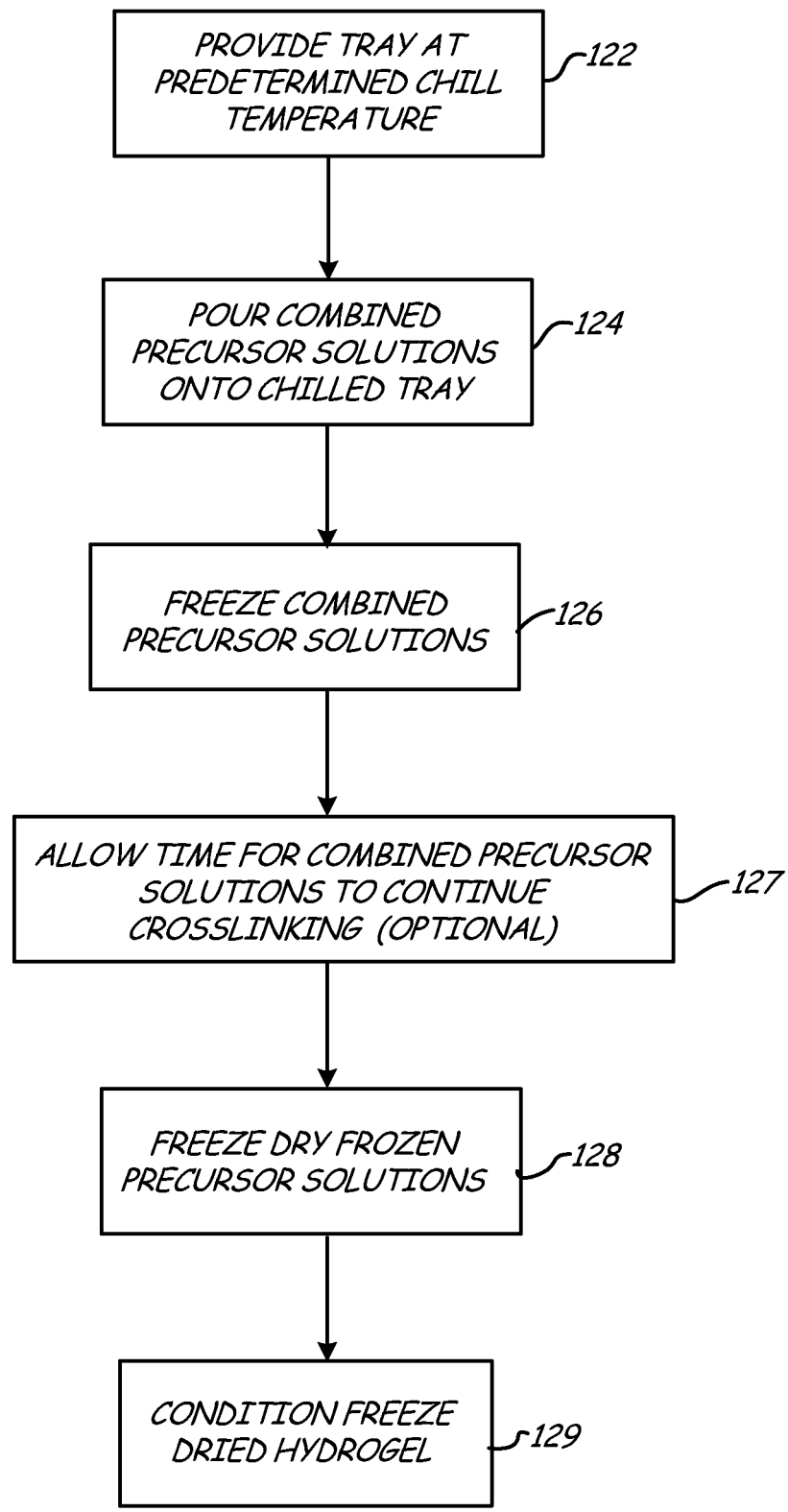

Turning to the drawings, FIGS. 1-3 show an exemplary method for making freeze dried hydrogel and/or for forming one or more structures from freeze dried hydrogel material that may be introduced into a body. Generally, the hydrogel may be a superabsorbent and/or biodegradable hydrogel formed using one or more of the processes described elsewhere herein. The hydrogel may be implanted or otherwise delivered into a patient's body, e.g., within tissue, a body lumen, or other location such that the hydrogel is exposed to bodily fluids or other aqueous environment, as described further elsewhere herein. As used herein, "superabsorbent" defines a hydrogel that rapidly absorbs fluid when exposed to an aqueous environment, e.g., that undergoes between about five hundred and three thousand percent (500-3000%) mass increase (wet weight gain v. dry weight) due to fluid absorption within about five to sixty (5-60) seconds of exposure to whole blood.

The hydrogel made using the methods described herein may have a density between about 0.05 and 0.30 grams per cubic centimeter (g/cc). Density, along with the precursor components and/or other process parameters, may affect one or more properties of the hydrogel material, e.g., rate of swelling, magnitude of swelling, compressive modulus, and the like. For example, the hydrogel may rapidly swell when exposed to an aqueous environment, e.g., swelling between about five hundred and three thousand percent (500-3000%) of the initial mass within about five to sixty (5-60) seconds ("rate of swelling"). In addition or alternatively, the hydrogel may expand between about five and fifty (5-50) times in volume from its dehydrated state after being formed to its fully hydrated state ("magnitude of swelling"). Once hydrated, the hydrogel may be absorbed or otherwise degrade within the body over a period of time, e.g., between about one and ninety (1-90) days or between about five and sixty (5-60) days. Alternatively, the hydrogel may be substantially non-degradable, i.e., may not substantially degrade within one or two years in a physiological environment.

The hydrogel formed using the materials and methods described herein may constitute a macroporous network, a microporous network or "foam," i.e., a two-phase solid-gas system that includes a solid lattice of material that is substantially continuous through the hydrogel. The gas phase (e.g., air) may be distributed substantially evenly through the lattice in voids or "pores." The foam may be "open-cell," i.e., the pores may include openings allowing fluid communication from one pore to another through the lattice defining the pores.

As shown in FIG. 1, a method for making a superabsorbent, biodegradable hydrogel, such as those described herein, generally includes three steps: combining two or more precursor materials to initiate creation of hydrogel material (step 110), freeze drying the hydrogel material (step 120), and forming the hydrogel material into one or more structures (step 130). The resulting structure(s) may subsequently be introduced into a patient's body, e.g., into a puncture, body lumen, or other passage through tissue, as described further below. Although the steps or substeps of the exemplary methods are described herein as being performed in a particular order, the steps may be provided in different sequences than those described.

Turning to FIG. 2, an exemplary method is shown for combining precursor materials, e.g., during step 110 of the method of FIG. 1. Initially, at step 112, polymer components may be provided in powder form, e.g., premanufactured by a supplier. In exemplary embodiments, the polymer components may include poly-ethyleneglycol (PEG) based molecules with reactive endgroups, polypeptides, etc. The reactive endgroups may encompass any set of chemical groups that may form a bond under specified environmental conditions, such as amine and/or ester end groups. Multiple types of base polymer (linear PEG of varying molecular weights, star PEG with varying numbers of arms and molecular weights, etc.) may be used.

In an exemplary embodiment, the powder components may simply be a two (2) part system. One example of such a system may include a single PEG-nucleophile and a single PEG-electrophile. The system may include formulations, such as those disclosed in U.S. Pat. No. 6,566,406 or 7,009,034, the entire disclosures of which are expressly incorporated by reference herein to the extent that they do not contradict what is explicitly disclosed herein. Examples of a suitable system may include a combination of branched electrophilic PEGs and one or more di-, tri-, or tetra-lysines, which have amine functional groups.

For instance, the system may include a first electrophilic precursor and a second nucleophilic precursor, such that the two precursors may be reacted with each other to form a crosslinked hydrogel. For example, a precursor may be a multi-armed PEG (e.g., with two to twelve (2-12) arms) with electrophilic or nucleophilic functional groups. Precursor weights may range significantly depending upon intended properties, e.g., with arms in the range of about five to one hundred kiloDaltons (5-100 kDa). Examples of electrophilic functional groups are succinimidyl glutarate (SG), carboxymethyl-hydroxybutyrate-N-hydroxysuccinimidyl (CM-HBA-NS), N-hydroxysuccinimides, maleimides, and succinimidyl esters. Examples of nucleophilic functional groups are amines and thiols.

The precursors may be chosen to include groups biodegradable by hydrolysis upon exposure to aqueous solution and/or by targeted enzymatic degradation by incorporating amino acid sequences intended to be degraded by enzymes relevant to the site of hydrogel application, e.g., collagenases. Examples of hydrolytically degradable groups are esters.

Alternatively, the powder components may be more complicated, i.e., including more than two powder components, e.g., a four (4) part system including a PEG-amine, a polypeptide, a low molecular weight PEG-ester, and a high molecular weight PEG-ester. Any combination of polymer components that may form a hydrogel may be provided for the initial polymer components.

At step 112, the powder components are individually weighed to a mass intended to give a desired percentage of solid polymeric material in the final hydrogel (after the powders are reconstituted and mixed together). For example, the powder components may be measured from a bulk container and placed into individual bottles or other containers. Alternatively, the powder components may be provided pre-measured to the desired masses in individual containers provided by the manufacturer.

At step 114, one or more buffer solutions may also be provided. For example, a specific buffer solution may be fabricated to facilitate the use of each of the individual polymer components, such as those described above. In exemplary embodiments, the buffer solutions may include a borate buffer (e.g., for an amine polymer powder component) and/or a phosphate buffer (e.g., for an ester polymer powder component).

The buffer solutions may be measured from one or more bulk containers or may be provided in individual containers, e.g., in an amount having a predetermined ratio with the amount of powder components corresponding to the respective buffer solutions. The buffering agent, molarity, and pH of each of the buffer solutions may be adjusted to achieve a desired gelation time (i.e., full crosslinking time) when the reconstituted polymer solutions are combined.

At step 116, the powder components may be reconstituted with the buffer solutions to create precursor solutions. In particular, each of the powder components may be reconstituted with their respective buffer solutions and stored in individual containers. For example, each of the buffer solutions may be poured into the respective containers including the corresponding powder components. The containers may then be shaken or otherwise mixed to substantially dissolve the powder components in the buffer solutions. Additional information on components for precursor solutions and methods for making them may be found in U.S. Pat. Nos. 6,152,943 and 6,606,294, the entire disclosures of which are expressly incorporated by reference herein.

Depending upon the compounds used for the powder components and buffer solutions, the reconstitution may be completed in advance of the balance of the process or immediately before completing the process. For example, some precursor solutions may remain substantially stable for an extended period of time after the powder components are reconstituted. Thus, such precursor solutions may be prepared in advance of completing the hydrogel process, e.g., hours or even days in advance. Conversely, other precursor solutions, such as those including PEG-esters, may need to be reconstituted immediately before use, because of the hydrolytic nature of PEG-esters, e.g., about one minute before completing the hydrogel process.

At step 118, after each of the precursor solutions are reconstituted, they may be combined together in a single container. As they are combined or after being combined, they may be thoroughly mixed to initiate a crosslinking reaction and creation of hydrogel material. The method of mixing may be chosen according to the types of polymer used and/or the total volume of precursor solutions used. For example, a relatively small volume of non-foaming material may be mixed using a centrifuge or vortex machine, which mixes the solutions with vibrational agitation. Alternatively, a large volume of precursor solutions may be mixed using a stir plate or other type of non-agitating mixing. Active mixing may be maintained for a predetermined mixing time, e.g., between about ten and sixty (10-60) seconds, to ensure that the combined precursor solutions are sufficiently mixed together.

Next, at step 119, the combined precursor solutions may be allowed to sit for a predetermined crosslinking duration, e.g., to allow the combined precursor solutions to at least partially crosslink.

In exemplary embodiments, the predetermined crosslinking duration may be between about half to two-and-a-half (0.5-2.5) minutes for a polymer solution with a full crosslinking time of about four to eight (4-8) minutes. This step may allow the combined precursor solutions to crosslink to a desired percentage of complete crosslinking before initiating the freeze drying process, e.g., between about one and ninety nine percent (1-99%), including about one to fifteen percent (1-15%), about five to twenty percent (5-20%), about ten to thirty percent (10-30%), about fifteen to forty percent (15-40%), about twenty to sixty percent (20-60%), about forty to eighty percent (40-80%), about fifty to ninety percent (50-90%), and sixty to ninety-nine (60-99%), of full crosslinking.

In one embodiment, the combined precursor solutions may be poured into a chilled tray or other container, as described above, and allowed to sit at substantially ambient temperatures. Alternatively, the tray may be maintained at the predetermined chill temperature, e.g., by placing the tray with the combined precursor materials therein in the freeze drying machine or a plate set at the predetermined chill temperature (but remaining at substantially ambient pressures). As the combined precursor solutions cool, the rate of crosslinking may slow and/or cease at a desired percentage before complete crosslinking has occurred.

In a further alternative, the tray may be initially provided at ambient temperature, and the combined precursor solutions may be allowed to sit at substantially ambient temperatures for the predetermined crosslinking duration or placed within the freeze drying machine or on a plate set at a desired temperature. In yet another alternative, the combined precursor solutions may be allowed to crosslink for the predetermined crosslinking duration before being poured onto the tray (which may or may not be chilled, as described above).

Returning to FIG. 1, once the precursor solutions are adequately mixed and/or at least partially crosslinked, the resulting hydrogel material may be freeze dried, at step 120, e.g., in a freeze drying machine. The freeze drying machine may be a conventional device including a chamber capable of being maintained at one or more desired temperatures and/or vacuum pressures for one or more desired periods of time. If the freeze drying process includes multiple sequential stages, i.e., each stage having a predetermined temperature, pressure, and/or duration, which may be controlled manually or preprogrammed into the freeze drying machine.

Turning to FIG. 3, an exemplary method is shown for freeze drying the combined precursor solutions and/or hydrogel material. Initially, at step 122, a freeze tray may be provided at a predetermined chill temperature. The predetermined chill temperature may be selected to provide a desired rate of cooling of the combined precursor solutions, e.g., between about negative twenty to seventy degrees Celsius (−20 to −70° C.). In an exemplary embodiment, the tray may be chilled to a temperature substantially equivalent to the initial freeze drying temperature, e.g., not warmer than about negative forty degrees Celsius (−40° C.). For example, the tray may be chilled at the chosen predetermined temperature by simply placing the tray on the freeze drying machine shelf for sufficient time to allow the tray to attain the freeze drying temperature of the freeze drying machine. Alternatively, the tray may be pre-chilled in a freezer, refrigerator, on a temperature-controlled plate, or other equipment.

At step 224, the combined precursor solutions and/or hydrogel material may be poured onto the tray. The tray may have any desired shape selected to provide a final shape for the hydrogel material that is to be formed into the one or more structures. For example, the tray may simply be a flat tray, e.g., having a round, rectangular, square, or other geometric shape. When the combined precursor solutions are poured onto the tray, they may assume a substantially uniform thickness across the bottom of the tray, e.g., between about one and twenty five millimeters (1-25 mm). Alternatively, the tray may include one or more recesses to create a predetermined varied thickness or three-dimensional configuration for the combined precursor solutions and/or final hydrogel material. In a further alternative, the tray may include multiple cavities into which the combined precursor solutions may be poured to create multiple structures onto the tray that are substantially isolated from one another.

Optionally, the tray may include one or more surface coatings, e.g., to facilitate removal of the hydrogel material from the tray before or after being formed into one or more structures, as described below. For example, surface coatings that are hydrophobic may be useful for this purpose, such as Teflon, silicone, Parylene, and the like.

In addition, the tray material (e.g., steel, aluminum, plastic, glass, etc.) may be selected to achieve desired process parameters and manufacturability. For example, an aluminum tray may cool quickly and has a high rate of heat transfer, while a Teflon tray may remain relatively unaffected by sudden changes in temperature. The tray design may include flanges, radiator like fins or other such features (not shown) that act as heat sinks to dissipate the heat of the liquid solution into the cold environment. Thus, the material and/or tray design may be selected to slow or accelerate chilling of the combined precursor solutions. In an alternative embodiment, the tray may be provided at substantially ambient temperatures when the combined precursor solutions are poured onto the tray, rather than chilling the tray in advance. This alternative may accelerate initial crosslinking as compared to using a chilled tray. Pouring onto a tray above the freeze temperature also allows the liquid mixture solution to self-level, resulting in a more uniform thickness.

At step 126, the combined precursor solutions (and/or at least partially crosslinked hydrogel material) may be cooled to a freezing temperature, i.e., below the freezing point of the combined precursor solutions, to freeze the combined precursor solutions and/or hydrogel material. For example, the tray may be placed in a controlled cold environment, e.g., a cold room or cold chamber, or on a temperature-controlled plate or other surface, thereby maintaining the tray at the freezing temperature for a predetermined time sufficient to freeze the combined precursor solutions.

Alternatively, the tray may be exposed to a freezing medium such as liquid nitrogen, which may freeze the combined solutions relatively quickly, or exposed to a freezing medium such as a dry ice and acetone solution for a predetermined time period. For example, the combined solutions may be "snap frozen," i.e., exposed to a freezing temperature sufficiently low to cause the temperature of the combined solutions to drop below the freezing temperature upon exposure to the freezing medium. Snap freezing may rapidly, substantially halt further crosslinking, while slower freezing stages may facilitate slow crosslinking over a longer period of time before substantially halting further crosslinking. If snap freezing is used, care should be taken to avoid cracks or other imperfections forming in the hydrogel material, e.g., which may occur when ice is created. During this step, the tray and hydrogel material may be maintained at substantially ambient pressures.

Optionally, if desired, at step 127, the frozen hydrogel may be held for a period of time before freeze drying, e.g., several days. This may allow additional crosslinking to occur, albeit at a much reduced rate, which may result in a more resilient structure after conditioning.

At step 128, once the hydrogel material is substantially completely frozen, the tray may be transferred to a freeze drying machine and the freeze drying process initiated. The process may include reducing the pressure within the freeze drying machine to a predetermined freeze drying vacuum (i.e., gauge pressure below ambient pressure) and/or maintaining the temperature within the freeze drying machine at a predetermined freeze drying temperature for one or more periods of time. The freeze drying process is halted once a desired amount of moisture is removed from the hydrogel material. The freeze drying step may be completed at a single pressure and/or temperature setting of the freeze drying machine.

Alternatively, the freeze drying step may be completed in multiple stages during which the pressure and/or temperature are adjusted in a desired manner to achieve the desired level of moisture removal, i.e., freeze drying of the hydrogel material. For example, during an initial stage, the tray may be maintained at a freeze drying temperature significantly below the freezing point of the combined precursor solutions, e.g., not more than about negative forty degrees Celsius (−40° C.), and at an appropriate application of vacuum pressure, e.g., a vacuum of about fifty milliTorr (50 mTorr), for about ten minutes (10 min.). Optionally, additional stages may be used to further control the freeze drying of the tray contents. For example, during a second stage, the tray may be maintained at a temperature slightly below the freezing point of the combined precursor solutions for an extended duration. Thereafter, during a third stage, the vacuum may be maintained at about fifty milliTorr (50 mTorr) while the temperature is slowly increased above the freezing point of the combined precursor solutions, e.g., at a rate of about ten degrees Celsius per hour (10° C./hr.) for about one hundred fifty minutes (150 min).

Optionally, additional stages may be used to further freeze dry the contents of the tray. For example, during a third stage, the tray may be maintained at a freeze drying temperature of not more than about negative twenty five degrees Celsius (−25° C.) and a vacuum of at least about fifty milliTorr (50 mTorr) for at least about 1,440 minutes. During a fourth stage, the temperature may again be raised, e.g., about ten degrees Celsius per hour (10° C./hr.), for about three hundred minutes (300 min.) at fifty milliTorr (50 mTorr) vacuum. Finally, during a fifth stage, the tray may be maintained at a temperature above the melt temperature of the combined precursor solutions for an extended duration while maintaining the appropriate application of vacuum pressure, e.g., at a temperature of not more than about twenty five degrees Celsius (25° C.) and a vacuum of at least about fifty milliTorr (50 mTorr) for at least about two hundred forty minutes (240 min.)

Next, with continued reference to FIG. 3, at step 129, upon termination of the freeze drying cycle, the freeze dried hydrogel material may be subjected to further environmental conditioning. Conditioning parameters, particularly temperature, may affect the final material with respect to thickness, density, porosity, and/or surface texture. For example, the hydrogel material may be subjected to one or more of the following: exposure to a controlled temperature and humidity environment, heat-assisted drying, exposure to an aerosolized buffer solution, vacuum assisted drying, and/or exposure to a controlled gas environment (argon, nitrogen, etc.). The hydrogel material may also be passed through different humidification and drying phases of environmental conditioning one or more times. For example, humidity may drive the reaction previously stopped by freeze drying the material to completion.

The freeze dried hydrogel may also be exposed to ambient temperature, pressure, and/or humidity conditions for an initial period (i.e., ambient temperatures, e.g., between about 20-25° C., ambient pressures, and/or ambient humidity, e.g., between about thirty and fifty percent (30-50%) relative humidity ("RH") for a first conditioning duration, e.g., at least about twenty four hours (24 hrs.). Thereafter, the temperature, pressure, and/or humidity may be increased (e.g., to at least about thirty five degrees Celsius (35° C.) and at least about ninety percent relative humidity (90% RH) for a second conditioning duration, e.g., at least about two hours (2 hrs.). Optionally, the hydrogel may be exposed to further conditioning stages at additional predetermined temperatures and/or humidities for predetermined durations to facilitate yield of hydrogel material with desired properties and morphology. For example, during a third stage, the hydrogel may be exposed to approximately thirty degrees Celsius (30° C.) and between about 20-30% RH for about two hours (2 hrs.), and during a fourth stage, the hydrogel may be exposed to ambient conditions (about 20-25° C.) and humidity between about 30-50% RH for at least about one hundred twenty hours (120 hrs).

During the one or more stages of conditioning, the hydrogel may complete further crosslinking before medical use. For example, in one embodiment, upon completing conditioning, the hydrogel material substantially completes crosslinking, e.g., to the extent that the hydrogel no longer has a substantial amount of unreacted ester end groups available for further crosslinking.

If desired, one or more tests may be completed to confirm that substantial crosslinking has occurred in a sample. For example, a fluorescent dye, e.g., fluorescein (which may have three primary amine groups that are likely to react with any unreacted ester groups in the sample), may be used to detect whether substantial unreacted reactive ester end groups remain within a sample. After applying the dye to the sample, the sample may be allowed sufficient time to react. The sample may then be rinsed to remove any excess dye, and the sample may be exposed to ultraviolet light. If the sample includes substantial unreacted reactive ester end groups, the dye will emit fluorescent light when exposed. Thus, if the sample is substantially completely crosslinked, i.e., includes substantially no unreacted reactive ester end groups, the dye will not fluoresce substantially when the sample is exposed to ultraviolet light.

Alternatively, it may be possible for substantially complete crosslinking during the freeze drying stage. For example, a highly branched active PEG may be mixed with trilysine, and freeze dried, e.g., using the one or more steps described elsewhere herein. Thus, a superabsorbent gel may be created simply by freeze drying.

Returning to FIG. 1, the freeze dried hydrogel material may then be machined or otherwise formed into its final form, in step 130. For example, the hydrogel material may be removed from the tray, and then cut, cored, machined, or otherwise sectioned into multiple structures, e.g., one or more sheets, rods, tubes, and the like. In addition or alternatively, the hydrogel material may be rolled, compressed, and/or folded into desired configurations or shapes. For example, the separate sections of the hydrogel material may be rolled, compressed, and/or folded into a configuration that may be loaded into a delivery device or otherwise sized for introduction into a patient's body, as described further below.

Exemplary Embodiment of the Process

For this example, a two polymer system is chosen. The system includes an amine terminated PEG and an ester terminated PEG. The polymer characteristics are given below:

Amine base polymer: 8 arm star PEG polymer, 20 kiloDalton total molecular weight Ester base polymer: 4 arm star PEG polymer, 10 kiloDalton total molecular weight.

The powder components are individually weighed to a mass that will result in five percent (5%) of the mass of the final hydrogel of existing as solid polymeric material.

Next, a borate buffer is chosen to reconstitute the amine polymer, and a phosphate buffer is chosen to reconstitute the ester polymer. The molarities and pH of these buffer solutions are chosen to optimize reactive conditions and working time of the materials after reconstitution, e.g., based upon the characteristics given below:

Borate Buffer: Sodium borate in water for injection
Molarity=0.05M
pH=7.63±0.05

Phosphate Buffer: Sodium phosphate in water for injection
Molarity=0.01M
pH=4.0±0.05.

Next, the PEG-amine is reconstituted with the borate buffer, and the PEG-ester is reconstituted with the phosphate buffer. The precursor solutions are then combined together, e.g., in a centrifuge tube and vigorously mixed, e.g. using a vortex machine, for about fifteen seconds (15 sec.).

Next, one or more trays or other containers with desired geometry/dimensions and surface coating/coatings, e.g., including a PTFE coating, may be chosen. The tray(s) may be readied for receiving the hydrogel precursor solutions by pre-chilling the tray(s) on the freeze dry machine shelf, which may be set to a predetermined freezing temperature. In an exemplary method, the tray area may be approximately five centimeters by five centimeters (5 cm×5 cm). The tray is chilled to about negative forty degrees Celsius (−40° C.) before use by allowing it to equilibrate on the shelf of the freeze drying machine.

Upon reaching the desired amount of crosslinking, a desired volume of the mixed precursor solutions is combined and allowed to reach the desired crosslinking, e.g. ninety seconds (90 sec) to achieve twenty five percent (25%) crosslinking with a six minute (6 min) solution, at which time about eight milliliters (8 ml) is then poured onto the chilled tray as it sits on the shelf of the freeze drying machine.

Immediately after the precursor solutions are poured onto the tray, the door to the freeze drying machine is sealed. The solutions are kept at this temperature for a minimum of two minutes (2 min). At this point, the freeze drying cycle is initiated. Typical freeze drying parameters known in the art may be employed such that the free and bound water are removed without causing substantial melt back of the polymer material. Exemplary parameters for freeze drying are listed below:

| Step | Shelf Temperature | Condenser Temperature (° C.) | Vacuum (mTorr) | Time (min) |
|---|---|---|---|---|
| 1 | Hold at −40° C. | −50 | 50 | 10 |
| 2 | Ramp temp at +10° C./hour | −50 | 50 | 150 |
| 3 | −25 C. | −50 | 50 | 1440 |
| 4 | Ramp temp at +10° C./hour | −50 | 50 | 300 |
| 5 | 25° C. | −50 | 50 | 240 |

Upon completing the freeze drying cycle, the crosslinked material is subjected to further environmental conditioning. Exemplary conditioning parameters are listed below:

| Step | Time (hours) | Parameters |
|---|---|---|
| 1 | ≥24 hours | Ambient conditions (~20-25° C., ~30-50% RH) |
| 2 | 2 hours | 35° C., 90% RH |
| 3 | 2 hours | 30° C., ~20-30% RH |
| 4 | ≥120 hours | Ambient conditions (~20-25° C., ~30-50% RH) |

The environmental parameters (temperature, pressure and/or humidity) to which the hydrogel is exposed may be adjusted, e.g., to change the output performance of the final freeze dried material relative to rate of hydration, magnitude of volume expansion, and post production shelf life, as explained elsewhere herein. Generally, upon completing these conditioning steps, the hydrogel material will be fully crosslinked to the extent that the hydrogel no longer has a substantial amount of unreacted ester end groups available for further crosslinking.

The freeze dried hydrogel is then cut to desired dimensions and/or mass. For example, the hydrogel may be formed into a size of about fifteen millimeters long by about six to eight millimeters wide by about one to one and a half millimeters thick (15 mm×6-10 mm×1.0-1.5 mm) with a target mass of about twenty milligrams (20 mg±6 mg). The material is then ready to be further processed for the desired medical application.

The resulting material may be formed into one or more structures for introduction and/or implantation into a body. The structures may be introduced into a body alone or as part of other devices for a variety of applications, e.g., through existing passages (e.g., blood vessels or other body lumens) or surgically created passages (e.g., punctures or other tracts through tissue), applied to biological surfaces, and the like. For example, the structures may be used for access site closure, embolic applications, e.g., to close or isolate arteriovenous malformations, aneurysms, tumor sites, and the like. The structures may be incorporated into other devices, e.g., to provide coatings on stents, neurovascular coils, drug delivery implants, or other implantable devices. The structures may also be incorporated into hemostatic patches or other devices that may be applied to surfaces within a body. The devices may be permanent or may be bioabsorbable such that the hydrogel and/or other components of the devices may be absorbed by the body over time. Exemplary devices and applications that may incorporated the methods and materials described herein are disclosed in U.S. Pat. No. 6,605,294, the entire disclosure of which is expressly incorporated by reference herein.

Figure 4:
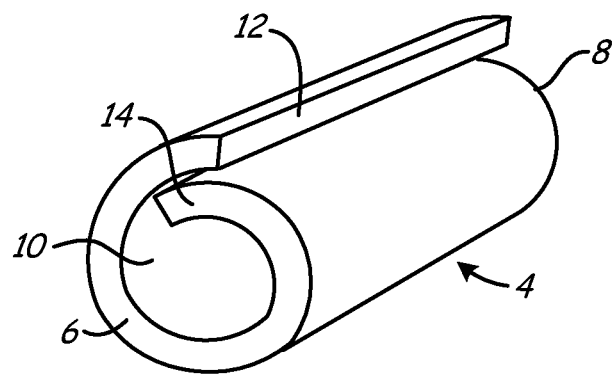
FIG. 4 is a perspective view of an exemplary structure that may be formed from a freeze dried hydrogel.

Turning to FIG. 4, an exemplary device or structure 4 is shown that may be formed from freeze dried hydrogel material, such as those resulting from the methods described above. For example, the structure 4 may be a plug or other hemostatic device that may be delivered into a puncture or other body lumen to substantially seal the body lumen.

To form the structure 4, a sheet or other section of hydrogel material cut from a larger portion may be rolled into a cylindrical shape having first and second ends 6, 8. The sheet may be rolled such that the structure 4 includes a central lumen 10 extending between the first and second ends 6, 8. For example, the sheet may be rolled such that longitudinal side edges 12, 14 of the sheet overlap one another, as shown. Alternatively, the side edges 12, 14 may be butted or connected to one another.

In a further alternative, the section may be rolled, machined, or otherwise formed into a solid rod or bar. If desired, a central lumen may be formed through such a rod or bar, e.g., by drilling, coring, and the like. In addition or alternatively, the section of hydrogel (whether rolled or not) may be compressed to provide a desired diameter or other cross-section. In exemplary embodiments, the resulting structure 4 may have a diameter between about 1.5-2.4 millimeters and/or a length between about thirteen to seventeen millimeters (13-17 mm). The lumen 10 may have a diameter between about 0.5-0.9 mm.

Optionally, the structure 4 may include one or more components to provide an adherent layer around the structure 4, e.g., one or more adherent layer precursors. In addition or alternatively, the adherent layer precursors may be infused or otherwise intermixed substantially throughout the structure 4. Additional information on such adherent layers may be found in application Ser. No. 10/982,387, filed Nov. 5, 2004, Ser. No. 10/982,384, and filed Nov. 5, 2004, the entire disclosures of which are expressly incorporated by reference herein.

In addition or alternatively, the structure 4 may include pro-thrombotic material, e.g., including one or more biological pro-thrombotics, such as collagen, fibrin, thrombin, carboxymethylcellulose, oxidized cellulose, alginates, gelatin, or other protein-based material, and/or synthetic materials, such as polyglycolic acids (PGA's), polyactides (PLA's), polyvinyl alcohol, and the like. Optionally, the structure 4 may include therapeutic and/or pharmaceutical agents, e.g., to treat particular disease conditions, promote healing, prevent infection and/or other adverse medical events, and the like. Such agents may be embedded in the material of the structure 4 after forming and/or applied as one or more coatings or layers. These agents may also be introduced either in the hydrogel fabrication process, e.g., to the powders before reconstitution, to the precursor solutions at the time of mixing, to the hydrogel cake at the time of conditioning, or at any time before its medical use.

Optionally, the structure 4 may include an agent for increasing the rate of uptake of a solution into the freeze dried hydrogel, e.g. to reduce surface tension of the pores and/or enhance closure efficacy. Such agents may be embedded in the material of the structure 4 after forming and/or applied as one or more coatings or layers. These agents may also be introduced either in the hydrogel fabrication process, e.g. to the powders prior to reconstitution, to the precursor solutions at the time of mixing, to the hydrogel cake at the time of conditioning, or any time before its medical use.

Optionally, the structure 4 may include a radiopaque agent to facilitate visualization of the hydrogel material under x-ray or commonly used fluoroscopic equipment. Such agents may be embedded in the material of the structure 4 after forming and/or applied as one or more coatings or layers. These agents may also be introduced either in the hydrogel fabrication process, e.g. to the powders prior to reconstitution, to the precursor solutions at the time of mixing, to the hydrogel cake at the time of conditioning, or any time before its medical use.

In another alternative, the structure 4 may be formed from a composite or laminate structure including two or more layers of hydrogel material (not shown). For example, each of the layers of hydrogel material may be formed as described above and laminated, molded, or otherwise formed together. Alternatively, a hydrogel material for a first layer may be poured or otherwise delivered onto a tray or other container, similar to the methods described elsewhere herein. The hydrogel material may be poured onto the tray in a liquid or fluid state such that it adopts the shape of or at least partially fills the tray. Before completing crosslinking of the hydrogel material, a second hydrogel material may be poured over the first layer to create a second layer over the first layer. The second layer may slightly penetrate into the first hydrogel layer, e.g., to enhance bonding or otherwise laminate the two layers.

The material for the second layer may be different from the material forming the first layer. Optionally, a third or additional layers may be applied over the second layer. In this regard, multiple distinct hydrogel layers may be created to form a laminate structure.

Before completing crosslinking of the second and/or additional layers, the tray may be frozen and then freeze dried, similar to the methods described elsewhere herein. The laminate may then be removed from the tray and shaped into a desired geometry, also as described elsewhere herein.

In yet another alternative, the hydrogel may modified with a blocking agent that substantially limits or prevents the hydrogel from swelling. The blocking agent may be transient in that it is removed via diffusion or in a fluid flow field allowing for consistent and delayed swelling as might be needed for medical applications that require repositioning or retrievability before permanent implantation and/or disconnection from a delivery device.

Figure 5:
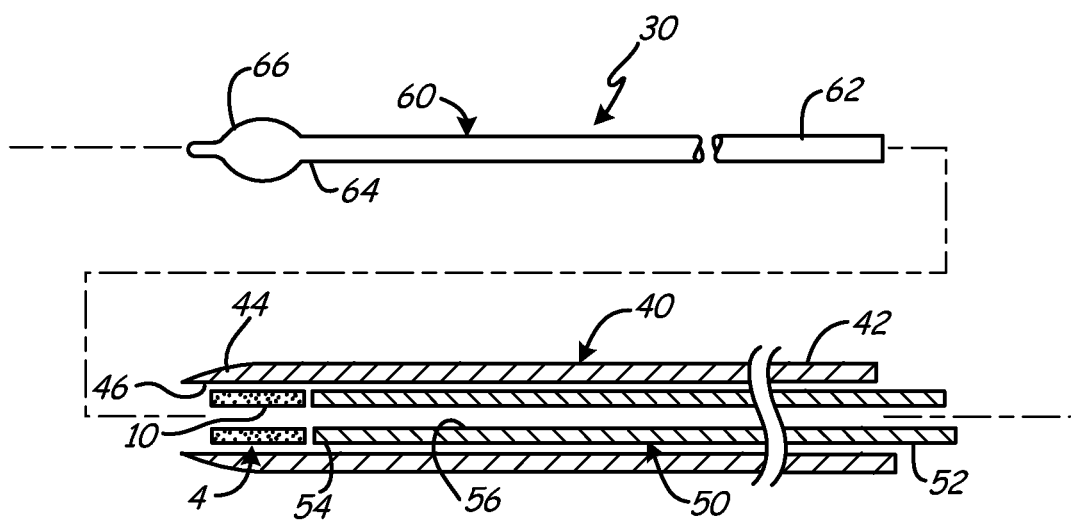
FIG. 5 is a perspective view of an exemplary delivery device for delivering a structure, such as that shown in FIG. 4, into a patient's body.
Figure 6A:
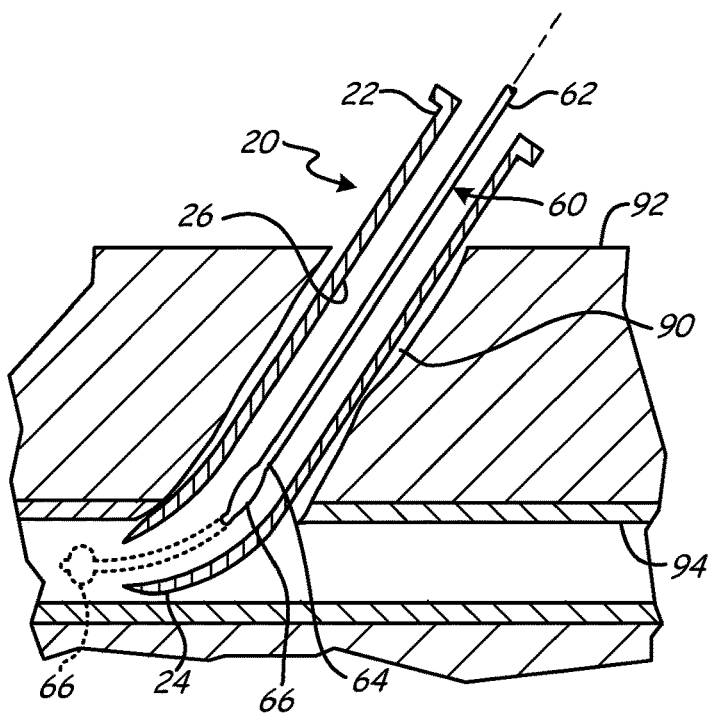
FIG. 6A is a cross-sectional view of the device of FIG. 5 in use, with the positioning element in the bodily lumen.
Figure 6B:
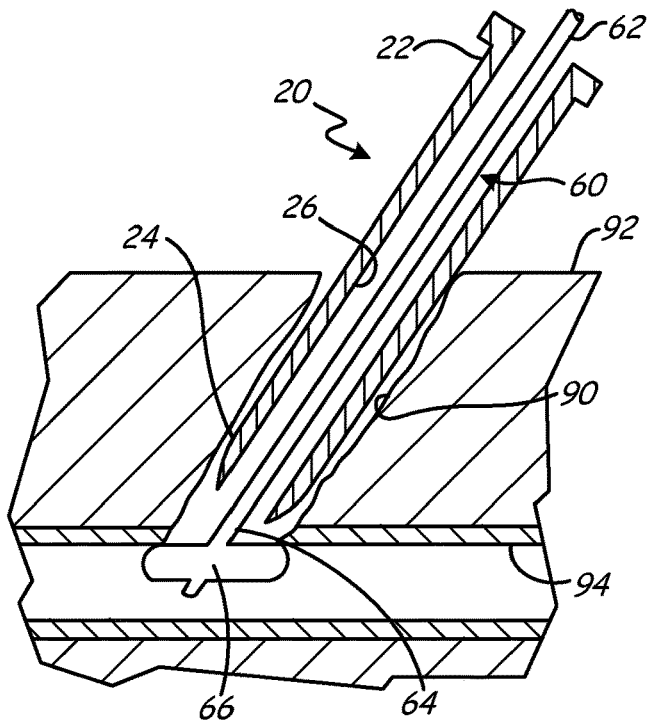
FIG. 6B is a cross-sectional view of the device of FIG. 5, with the positioning element in a sealing position in the bodily lumen.
Figure 6C:
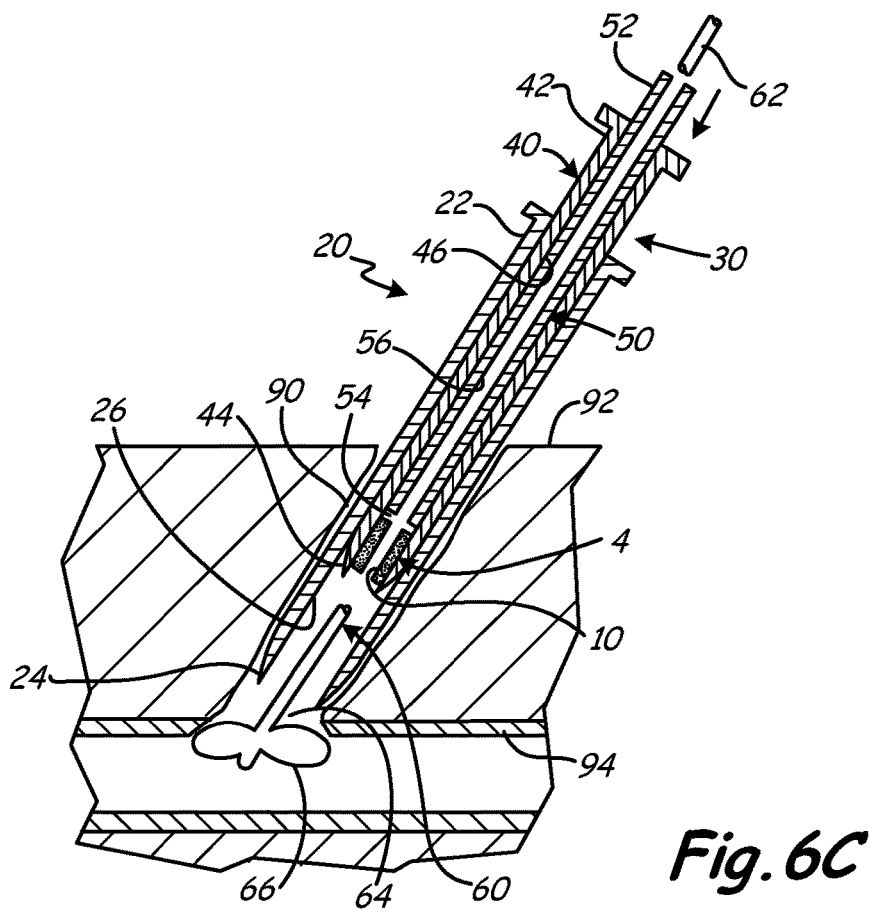
FIG. 6C is a cross-sectional view of the device of FIG. 5, with a delivery sheath in place in the bodily lumen.
Figure 6D:
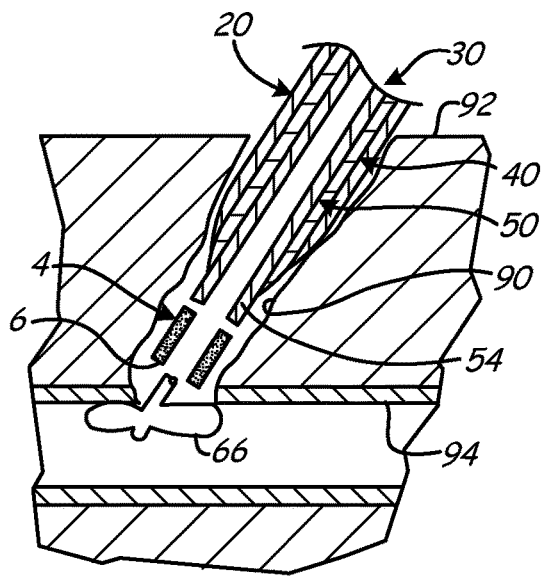
FIG. 6D cross-sectional view of the device of FIG. 5, with structure 4 outside of the sheath in the bodily lumen.
Figure 6E:
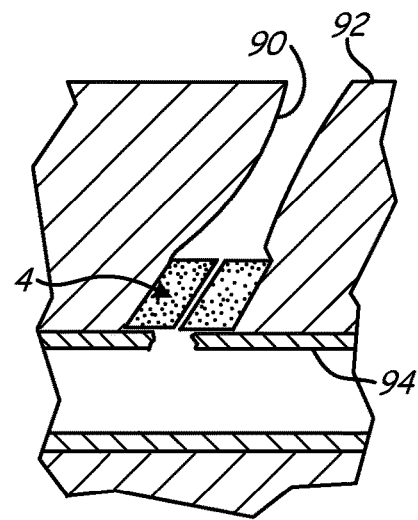
FIG. 6E is a cross-sectional view of structure 4 as delivered with the device of FIG. 5 in the bodily lumen.

Turning to FIG. 5, a delivery cartridge, catheter, or other apparatus 30 may be provided for delivering the structure 4 of FIG. 4 (or other configuration for the structure 4), e.g., for sealing a puncture or other body lumen. Generally, the apparatus 30 may include a delivery sheath or other tubular member 40, a plunger or other pusher member 50, and, optionally, a positioning member 60.

The delivery sheath 40 may be a substantially rigid, semi-rigid, or flexible member including a proximal end 42, a distal end 44 sized for introduction into a body lumen or other passage through tissue, and a lumen 46 sized to receive or otherwise carry the structure 4 therein. The distal end 44 may be tapered and/or may include a substantially atraumatic tip to facilitate advancement through a tissue passage. The delivery sheath 40 may include a handle (not shown), and/or one or more seals, e.g., a hemostatic seal (also not shown), on the proximal end 42. The structure 4 may be disposed within the lumen 46, e.g., adjacent the distal end 44. The lumen 42 may be sized such that the structure 4 is slidable therein, e.g., able to traverse distally from the delivery sheath 40 during delivery, as described further below.

The pusher member 50 may be an elongate member, e.g., a plunger, catheter, and the like, including a proximal end 52 and a distal end 54 sized for slidable insertion into the lumen 42 of the delivery sheath 40. Optionally, the proximal end 52 of the pusher member 50 may include a connector (not shown) for coupling the lumen 54 of the pusher member 50 to a syringe or other delivery device 70 (also not shown) for delivering one or more fluids into or through the apparatus 30. Additional information on other components, alternative apparatus, and methods for using them may be found in co-pending application Ser. No. 10/806,952, filed Mar. 22, 2004, and Ser. No. 10/982,384, filed Nov. 5, 2004, the disclosures of which are expressly incorporated by reference herein.

Still referring to FIG. 5, the distal end 54 of the pusher member 50 may be substantially blunt to facilitate contacting, tamping, pushing, and/or "cinching" the structure 4 within the delivery sheath 40 and/or a passage, as described further below. The pusher member 50 may be substantially rigid, semi-rigid, and/or substantially flexible, having sufficient column strength to allow movement of the delivery sheath 40 relative to the structure 4 without buckling the pusher member 50. In one embodiment, the pusher member 50 has sufficient column strength to tamp down the structure 4 but retains a flexible or "floppy" distal end 52 to prevent accidental advancement of the structure 4 into a vessel or other body lumen 94. The pusher member 50 may also include a lumen 56 extending between the proximal end 52 and the distal end 54, e.g., to accommodate the positioning member 60 and/or a guidewire (not shown).

Optionally, as in the embodiment shown in FIG. 5, the positioning member 60 is a solid or hollow elongate body, including a proximal end 62, a distal end 64, and a positioning element 66 on the distal end 64. The positioning element 66 may be an expandable element, such as a balloon, a wire mesh structure, an expandable frame, and the like, such as those disclosed in application Ser. No. 10/982, 384, incorporated by reference above. The positioning element 66 may be selectively expanded or otherwise actuated from the proximal end 62 of the positioning member 60, e.g., using a source of inflation media, a pullwire, and/or other actuator (not shown). For example, a syringe or other source of inflation media may be coupled to a lumen (not shown) extending through the positioning member 60 to an inflatable positioning element. Additional information on expandable structures that may be incorporated into positioning member 60 may be found in U.S. Pat. Nos. 6,238,412 and 6,635,068, in co-pending application Ser. No. 10/143,514, published as Publication No. US 2003/0078616 A1, and Ser. No. 10/454,362, filed Jun. 4, 2003, Ser. No. 10/806,927, filed Mar. 22, 2004, Ser. No. 10/928,744, filed Aug. 27, 2004, and Ser. No. 11/112,971, filed Apr. 22, 2005. The entire disclosures of these references are expressly incorporated herein by reference.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

The invention claimed is:

1. A method for making superabsorbent hydrogel, comprising:
    forming a mixture in liquid media by combining precursor components to initiate covalent crosslinking of the precursor components, with the precursor components reaction having a full crosslinking time from 4 to 8 minutes if the reaction is allowed to achieve 100% crosslinking;
    snap freezing the mixture to stop the crosslinking reaction after the covalent crosslinking of the precursor components has begun and before crosslinking of the precursor components is complete, wherein between 15% and 90% of the crosslinking is completed prior to snap freezing the mixture; and
    freeze drying the frozen mixture to form the hydrogel.

2. The method of claim 1, further comprising conditioning the hydrogel after freeze drying.

3. The method of claim 2, wherein the hydrogel has substantially no unreacted reactive ester end groups after the hydrogel is conditioned.

4. The method of claim 1, wherein the precursor components comprise a first electrophilic precursor and a second nucleophilic precursor.

5. The method of claim 1 comprising, before the snap freezing, placing the combined precursor components onto a chilled tray or container.

6. The method of claim 1, further comprising forming the freeze dried hydrogel into one or more structures.

7. The method of claim 6, wherein the one or more structures are formed by at least one of cutting, machining, rolling, coring, and compressing the hydrogel.

8. The method of claim 6, wherein the one or more structures comprise a structure that is sized for introduction into a tissue tract leading to a blood vessel.

9. The method of claim 1, wherein crosslinking of the precursor components is initiated in an aqueous phase.

10. The method of claim 1, wherein the precursor components comprise a highly branched active PEG.

11. The method of claim 10, wherein the precursor components further comprise an oligopeptide with two or more lysine groups.

12. The method of claim 5, wherein placing the combined precursor components onto the chilled tray or container comprises pouring the combined precursor components into at least one recess of the chilled tray or container.

13. The method of claim 4 wherein the first electrophilic precursor comprises a multi-armed poly-ethylene glycol with 2-12 arms with electrophilic functional groups.

14. The method of claim 13 wherein the electrophilic end groups comprise a N-hydroxysuccinimide or a succinimidyl ester.

15. The method of claim 14 wherein the second nucleophilic precursor comprises a multi-armed poly-ethylene glycol with 2-12 arms with nucleophilic functional groups.

16. The method of claim 15 wherein the nucleophilic functional groups comprise amines.

17. The method of claim 14 wherein the second nucleophilic precursor is a dilysine, trilysine, or a tetralysine.

18. The method of claim 1, wherein the hydrogel comprises an open-cell hydrogel.

19. The method of claim 1, wherein the hydrogel is biodegradable.

20. The method of claim 1, wherein the hydrogel is substantially non-degradable.

21. The method of claim 1, wherein the hydrogel includes groups biodegradable by hydrolysis upon exposure to aqueous solution.

22. The method of claim 1, wherein the hydrogel has a density between 0.05 and 0.30 grams per cubic centimeter (g/cc).

23. The method of claim 1, wherein the hydrogel has a magnitude of expansion between about five and fifty (5-50) times the initial volume when exposed to an aqueous environment.

24. The method of claim 1, wherein between 40% and 80% of the crosslinking is completed prior to snap freezing the mixture.

* * * * *